United States Patent
Amit et al.

(10) Patent No.: US 9,874,527 B2
(45) Date of Patent: Jan. 23, 2018

(54) REMOVING PROCESS-VARIATION-RELATED INACCURACIES FROM SCATTEROMETRY MEASUREMENTS

(71) Applicant: KLA-Tencor Corporation, Milpitas, CA (US)

(72) Inventors: Eran Amit, Haifa (IL); Zeev Bomzon, Kiryat Tivon (IL); Barak Bringoltz, Rishon LeTzion (IL); Boris Efraty, Carmiel (IL)

(73) Assignee: KLA-Tencor Corporation, Milpitas, CA (US)

(*) Notice: Subject to any disclaimer, the term of this patent is extended or adjusted under 35 U.S.C. 154(b) by 180 days.

(21) Appl. No.: 14/797,754

(22) Filed: Jul. 13, 2015

(65) Prior Publication Data
US 2015/0316490 A1    Nov. 5, 2015

Related U.S. Application Data

(63) Continuation of application No. PCT/US2014/052670, filed on Aug. 26, 2014.

(60) Provisional application No. 61/870,233, filed on Aug. 27, 2013, provisional application No. 62/014,929, filed on Jun. 20, 2014.

(51) Int. Cl.
| | | |
|---|---|---|
| G01B 11/00 | (2006.01) | |
| G01N 21/88 | (2006.01) | |
| G01N 21/47 | (2006.01) | |
| G03F 7/20 | (2006.01) | |

(52) U.S. Cl.
CPC ......... *G01N 21/8851* (2013.01); *G01N 21/47* (2013.01); *G03F 7/70633* (2013.01)

(58) Field of Classification Search
CPC . G01N 21/8851; G01N 21/47; G03F 7/70633
USPC ........................................................ 356/400
See application file for complete search history.

(56) References Cited

U.S. PATENT DOCUMENTS

| | | | |
|---|---|---|---|
| 6,897,956 B2* | 5/2005 | Noguchi .............. | G01B 11/272 356/400 |
| 2004/0101769 A1* | 5/2004 | Hassmann .......... | G03F 7/70633 430/22 |
| 2007/0279630 A1 | 12/2007 | Kandel et al. | |

(Continued)

FOREIGN PATENT DOCUMENTS

| | | |
|---|---|---|
| WO | 2010115686 A1 | 10/2010 |
| WO | 2011012624 A1 | 2/2011 |
| WO | 2013079270 A1 | 6/2013 |

*Primary Examiner* — Hina F Ayub
(74) *Attorney, Agent, or Firm* — Suiter Swantz pc llo

(57) ABSTRACT

Metrology methods and respective software and module are provided, which identify and remove measurement inaccuracy which results from process variation leading to target asymmetries. The methods comprise identifying an inaccuracy contribution of process variation source(s) to a measured scatterometry signal (e.g., overlay) by measuring the signal across a range of measurement parameter(s) (e.g., wavelength, angle) and targets, and extracting a measurement variability over the range which is indicative of the inaccuracy contribution. The method may further assume certain functional dependencies of the resulting inaccuracy on the target asymmetry, estimate relative donations of different process variation sources and apply external calibration to further enhance the measurement accuracy.

19 Claims, 7 Drawing Sheets

(56) References Cited

U.S. PATENT DOCUMENTS

| | | |
|---|---|---|
| 2008/0074666 A1 | 3/2008 | Boef et al. |
| 2008/0239318 A1 | 10/2008 | Den Boef et al. |
| 2009/0073448 A1 | 3/2009 | Tenner et al. |
| 2009/0296075 A1* | 12/2009 | Hu .................. G03F 7/70633 356/73 |
| 2011/0001978 A1 | 1/2011 | Smilde et al. |
| 2011/0131538 A1 | 6/2011 | Ku et al. |
| 2011/0134419 A1 | 6/2011 | Fuchs et al. |
| 2011/0178785 A1 | 7/2011 | Tinnemans et al. |
| 2011/0255066 A1 | 10/2011 | Fuchs et al. |
| 2011/0292365 A1 | 12/2011 | Cramer et al. |
| 2012/0019816 A1* | 1/2012 | Shibata ................ G01N 21/21 356/237.5 |
| 2013/0016346 A1* | 1/2013 | Romanovsky ..... G01N 21/9501 356/237.5 |
| 2013/0054186 A1 | 2/2013 | Den Boef |
| 2014/0060148 A1* | 3/2014 | Amit ................... G01B 21/042 73/1.79 |

* cited by examiner

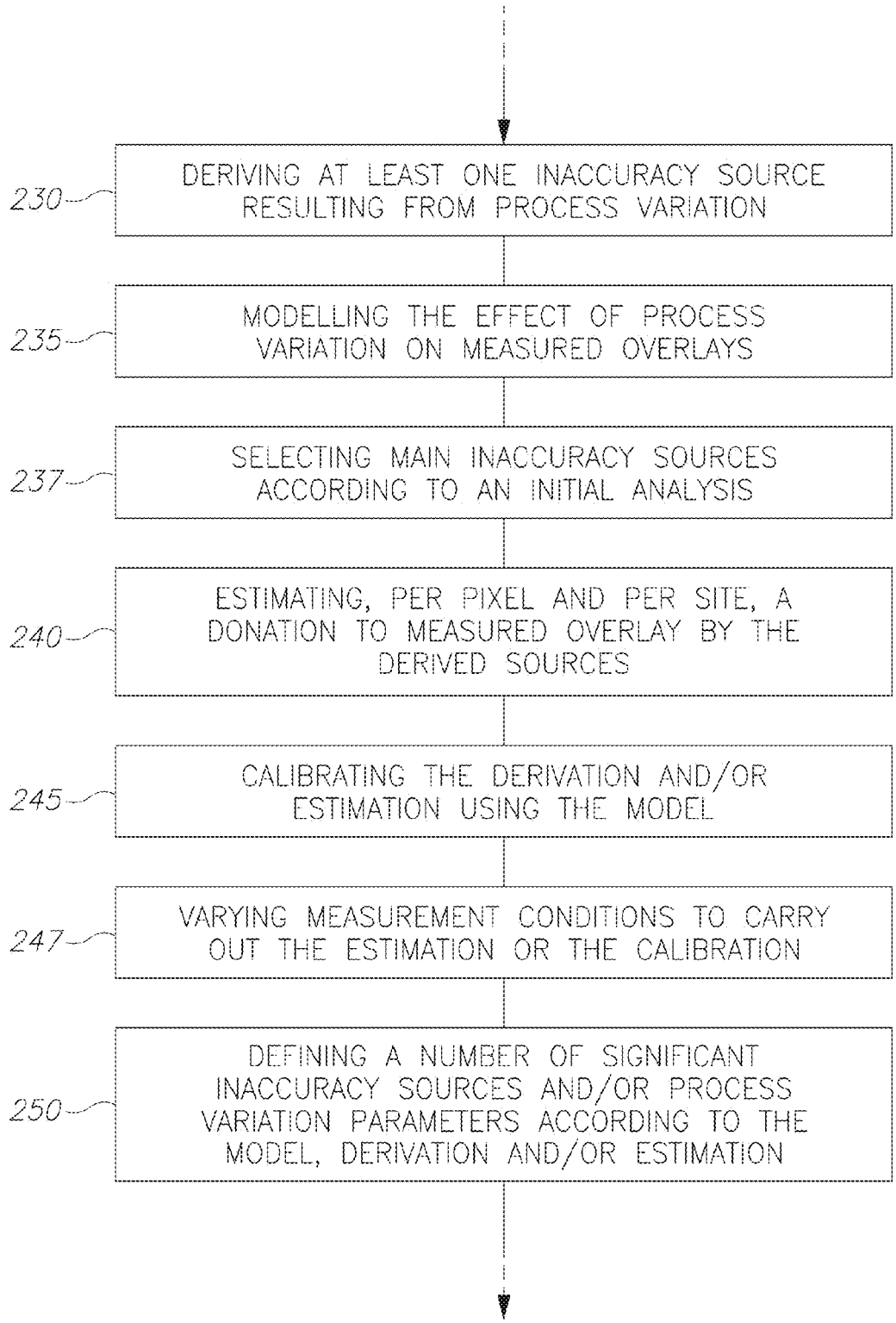
Figure 5 (cont. 1)

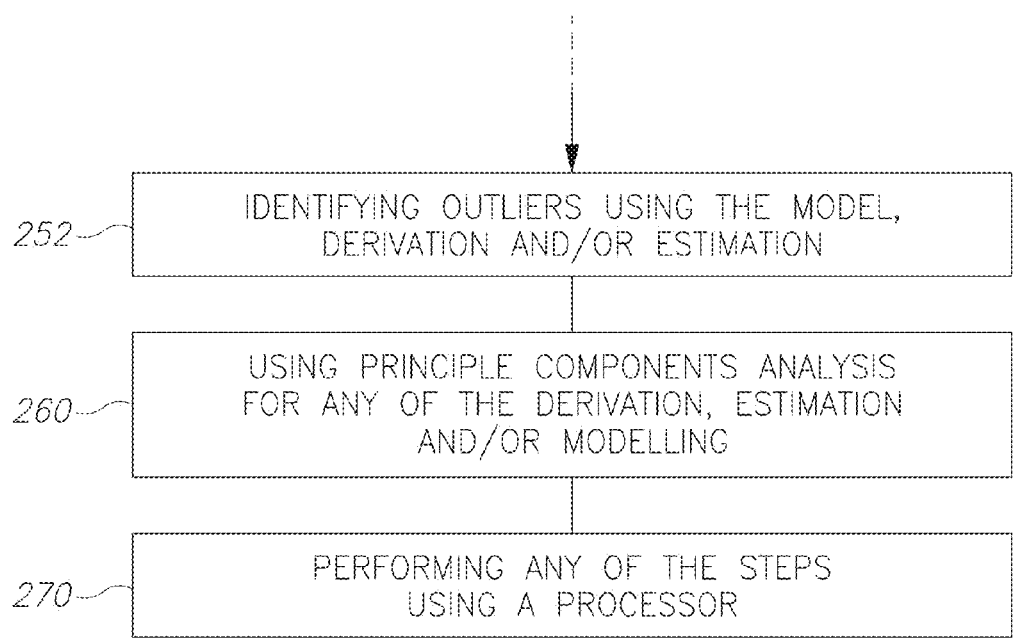
Figure 5 (cont. 2)

REMOVING PROCESS-VARIATION-RELATED INACCURACIES FROM SCATTEROMETRY MEASUREMENTS

CROSS REFERENCE TO RELATED APPLICATIONS

This application is filed under 35 U.S.C. § 111(a) and § 365(c) as a continuation of PCT International Patent Application No. PCT/US2014/052670, filed Aug. 26, 2014, which application claims the benefit of U.S. Provisional Patent Application No. 61/870,233 filed on Aug. 27, 2013 and U.S. Provisional Patent Application No. 62/014,929 filed on Jun. 20, 2014, which applications are incorporated herein by reference in their entireties.

BACKGROUND OF THE INVENTION

1. Technical Field

The present invention relates generally to the field of metrology, and, more particularly, to scatterometry metrology.

2. Discussion of Related Art

The following documents disclose various aspects of related art, and are incorporated herein by reference in their entireties.

U.S. Patent Publication No. 2008/0074666 discloses detecting both the 1st and 0th diffraction orders using a scatterometer. The 1st diffraction orders are used to detect the overlay error. The 0th diffraction order is then used to flag whether there is a false overlay error calculation of magnitude greater than the bias, but smaller than the pitch of the grating. Unfortunately, U.S. Patent Publication No. 2008/0074666 does not attempt to calculate inaccuracy.

U.S. Patent Publication No. 2013/0054186 discloses a metrology method comprising the steps of measuring scattering properties of a first target comprising a first structure and a second structure, constructing a model of the first structure using the measured scattering properties, the model comprising a first model structure corresponding to the first structure, modifying the model by overlaying the first model structure with an intermediate model structure, further modifying the model by replacing the intermediate model structure with a second model structure, corresponding to the second structure, calculating a second defect-induced overlay error between the first model structure and the second model structure, the first and second model structures being overlaid with respect to each other in the further modified model and determining an overlay error in a second target using the calculated second defect-induced overlay error. U.S. Patent Publication No. 2013/0054186 measures each grating separately, models it and finds the inaccuracy due to target imperfections.

WIPO Publication No. 2010/115686 discloses a method for the determination of an overlay error between two successive layers produced by a lithographic process on a substrate by using the lithographic process to form at least one periodic structure of a same pitch on each of the layers. One or more overlaid pairs of the periodic structures are formed in parallel, but offset relative to each other. A spectrum, produced by directing a beam of radiation onto the one or more pairs of periodic structures is measured. One or more portions of the spectrum are determined in which the relationship between the offset between the one or more pairs of periodic structures and the resultant variation in measured intensity of the spectrum at the one or more portions is more linear than the relationship outside the one or more portions. The offset between the one or more pairs of periodic structures on the basis of intensity measurements of the spectrum in the one or more portions of the spectrum is determined and used to determine the overlay error. WIPO Publication No. 2010/115686 applies the correction to future measurements, selects only a part of the spectrum, and neglects possible correlations between different pixels.

U.S. Patent Publication No. 2009/0073448 discloses the detection of the reflected radiation from a target mark including, for example, a plurality of gratings by an array of pixels. The overlay error of the gratings for each pixel is detected, and an array of overlay errors is determined. Rather than simply averaging the overlay error value for all the pixels, filtering is performed. Pixels may be filtered according to the detected value of the overlay error or the detected intensity of the pixel. U.S. Patent Publication No. 2009/0073448 uses model-based calibration which, if the imperfections are random, requires a separate model for each measurement. Further, it selects only a part of the spectrum and neglects possible correlations between different pixels.

U.S. Patent Publication No. 2011/0134419 discloses a method and associated apparatus to determine an overlay error on a substrate. A beam is projected onto three or more targets. Each target includes first and second overlapping patterns with predetermined overlay offsets on the substrate. The asymmetry of the radiation reflected from each target on the substrate is measured. The overlay error not resultant from the predetermined overlay offsets is determined. The function that enables calculation of overlay from asymmetry for other points on the wafer is determined by limiting the effect of linearity error when determining the overlay error from the function.

WIPO Publication No. 2013/079270 discloses an inspection method and corresponding apparatus enabling classification of pupil images according to a process variable. The method comprises acquiring diffraction pupil images of a plurality of structures formed on a substrate during a lithographic process. A process variable of the lithographic process was varied between formation of the structures, the variation of the process variable resulting in a variation in the diffraction pupil images. The method further comprised determining at least one discriminant function for the diffraction pupil images, the discriminant function being able to classify the pupil images in terms of the process variable. WIPO Publication No. 2013/079270 finds the process conditions of the wafers, but not the accuracy per target.

U.S. Patent Publication No. 2008/0239318 discloses a method of measuring asymmetry in a scatterometer where a target portion is illuminated twice, first with 0° of substrate rotation and secondly with 180° of substrate rotation. One of those images is rotated and then that rotated image is subtracted from the other image. In this way, asymmetry of the scatterometer can be corrected. U.S. Patent Publication No. 2008/0239318 finds the tool induced shift.

U.S. Patent Publication No. 2011/0292365 discloses methods, apparatuses, and lithographic systems for calibrating an inspection apparatus. Radiation is projected onto a pattern in a target position of a substrate. By making a plurality of measurements of the pattern and comparing the measured first or higher diffraction orders of radiation reflected from the pattern of different measurements, a residual error indicative of the error in a scatterometer may be calculated. This error is an error in measurements of substrate parameters caused by irregularities of the scatterometer. The residual error may manifest itself as an asymmetry in the diffraction spectra. U.S. Patent Publication No. 2011/0292365 uses multiple measurements in multiple measurement conditions for calibration per target.

U.S. Patent Publication No. 2011/001978 discloses a method for determining an overlay error between two successive layers produced by a lithographic process on a substrate, including using the lithographic process to form a calibration structure including a periodic structure of the same pitch on each of the layers, such that an overlaid pair of periodic structures is formed, the structures being parallel, but offset relative to each other by an overlay amount. A spectrum produced by directing a beam of radiation onto the calibration structure is measured and compared with one or more modeled spectra so as to determine values of the grating parameters for the calibration structure from the measured spectrum. The lithographic process is used to form further overlaid periodic structures on the same or one or more subsequent substrates, the determined grating parameter values for the calibration structure being used to determine overlay amounts for the further overlaid periodic structures. U.S. Patent Publication No. 2011/001978 uses modeling (such as RCWA-based modeling) of calibration targets and compares the measurements to the calculated per pixel overlay/asymmetry.

WIPO Publication No. 2011/012624 discloses a method of determining the focus of a lithographic apparatus used in a lithographic process on a substrate, the lithographic process is used to form a structure on the substrate, the structure having at least one feature which has an asymmetry in the printed profile which varies as a function of the focus of the lithographic apparatus on the substrate. A first image of the periodic structure is formed and detected while illuminating the structure with a first beam of radiation, the first image being formed using a first part of non-zero order diffracted radiation. A second image of the periodic structure is formed and detected while illuminating the structure with a second beam of radiation. The second image is formed using a second part of the non-zero order diffracted radiation which is symmetrically opposite to the first part in a diffraction spectrum. The ratio of the intensities of the measured first and second portions of the spectra is determined and used to determine the asymmetry in the profile of the periodic structure and/or to provide an indication of the focus on the substrate. In the same instrument, an intensity variation across the detected portion is determined as a measure of process-induced variation across the structure. A region of the structure with unwanted process variation can be identified and excluded from a measurement of the structure. WIPO Publication No. 2011/012624 uses sensitive features to identify focus/process-induced variations across the wafer, and not the inaccuracy in nm.

U.S. Patent Publication No. 2011/0178785 discloses a method for the calibration of an angularly resolved scatterometer is performed by measuring a target in two or more different arrangements. The different arrangements cause radiation being measured in an outgoing direction to be different combinations of radiation illuminating the target from ingoing directions. A reference mirror measurement may also be performed. The measurements and modeling of the difference between the first and second arrangements is used to estimate separately properties of the ingoing and outgoing optical systems. The modeling may account for symmetry of the respective periodic target. The modeling typically accounts for polarizing effects of the ingoing optical elements, the outgoing optical elements and the respective periodic target. The polarizing effects may be described in the modeling by Jones calculus or Mueller calculus. The modeling may include a parameterization in terms of basis functions such as Zernike polynomials. U.S. Patent Publication No. 2011/0178785 uses multiple measurement conditions to calibrate the optical system, rather than the target.

U.S. Patent Publication No. 2011/0255066 discloses an apparatus that measures properties, such as overlay error, of a substrate divided into a plurality of fields. The apparatus includes a radiation source configured to direct radiation onto a first target of each field of the substrate. Each first target (T4G) has at least a first grating and a second grating having respective predetermined offsets, the predetermined offset (+d) of the first grating being in a direction opposite the predetermined offset (−d) of the second grating. A detector is configured to detect the radiation reflected from each first target and to obtain an asymmetry value for each first target from the detected radiation. Further, a module is configured to determine an overlay value for each first target based on at least the obtained asymmetry value and the predetermined offsets and determine a polynomial fit across a plurality of first targets of a corresponding plurality of fields of the substrate for a relationship between the obtained asymmetry value and determined overlay value of each first target. U.S. Patent Publication No. 2011/0255066 uses four-cell targets to find a relation between differential signal and OVL and uses this relation to extract OVL from two-cell targets, and does not deal with target asymmetry and measurement inaccuracy.

Typically, the overlay measurements and, specifically, the scatterometry algorithm are very sensitive to process variations. Acceptable process variations (which do not affect the device performance) may be wrongly reported as unacceptable overlay errors. Therefore, there has been a long felt need for metrology methods to reduce this inaccuracy.

SUMMARY OF THE INVENTION

One aspect of the present invention provides a method comprising identifying an inaccuracy contribution of at least one process variation source to a measured scatterometry signal by measuring the signal across a range of at least one measurement parameter and plurality of targets and extracting a measurement variability over the range which is indicative of the inaccuracy contribution. At least one of the identifying, measuring, and extracting can be carried out by at least one computer processor.

The present invention also comprises a metrology module configured to measure a signal from a plurality of targets across a range of at least one measurement parameter, identify an inaccuracy contribution of at least one process variation source to a measured scatterometry signal, and extract a measurement variability over the range which is indicative of the inaccuracy contribution The present invention also comprises a computer-based apparatus, comprising: a memory element configured to store a plurality of computer-readable instructions; a processor configured to execute the plurality of computer-readable instructions to: measure a signal from a plurality of targets across a range of at least one measurement parameter; identify an inaccuracy contribution of at least one process variation source to a measured scatterometry signal; and, extract a measurement variability over the range which is indicative of the inaccuracy contribution.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION OF THE INVENTION

Figure 1:
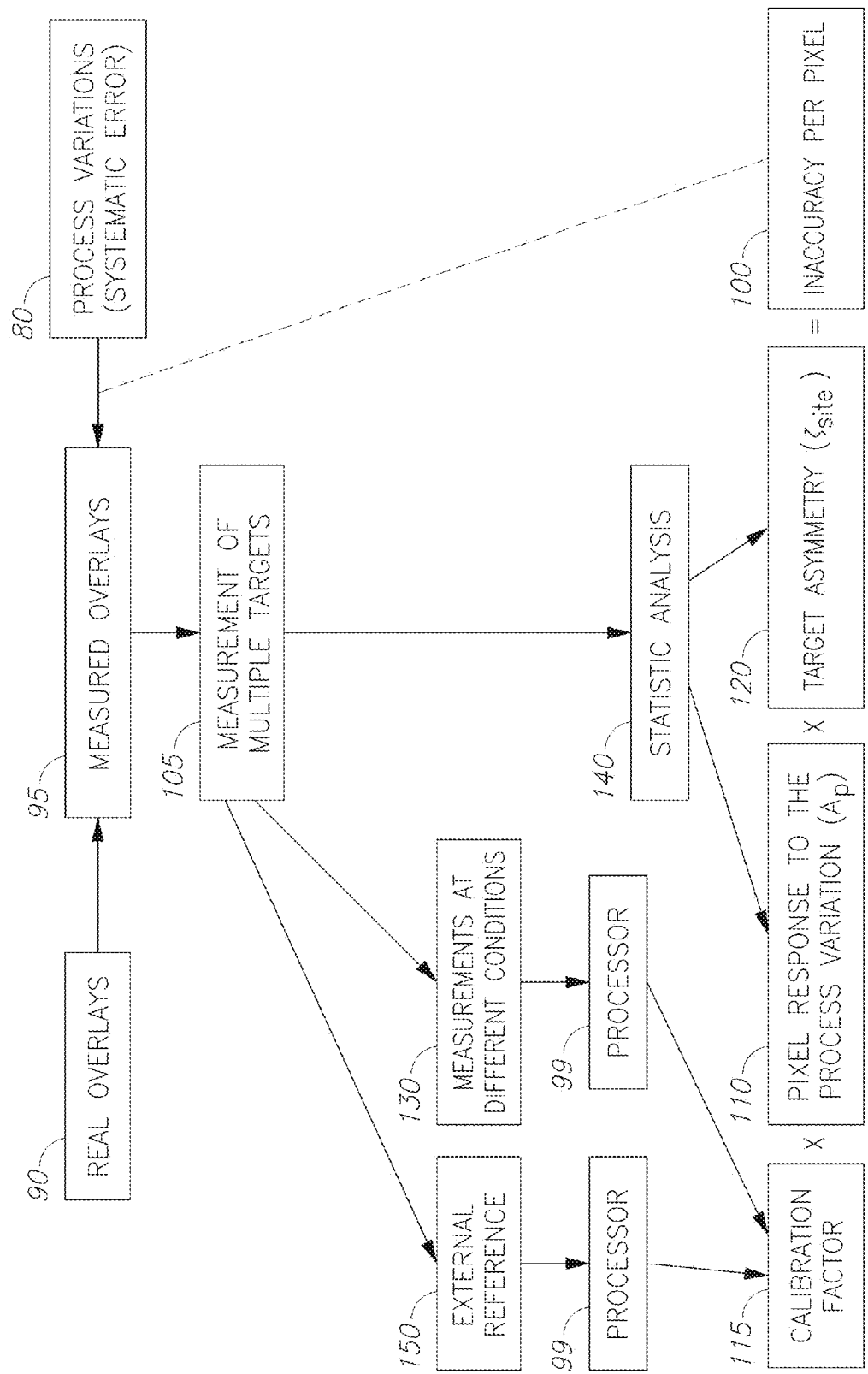
FIG. 1 is a high level schematic block diagram illustrating ways to reduce the inaccuracy arising from process variation in scatterometry overlay measurements, according to some embodiments of the invention.

Prior to the detailed description being set forth, it may be helpful to set forth definitions of certain terms that will be used hereinafter.

The term "process variation" as used in this application refers to any changes in the manufacturing process which result in inaccurate production of metrology targets (also referred to in the following as target asymmetries), resulting in signal measurements which are different from the actual physically expected signal.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Metrology methods and respective software and module are provided, which identify and remove measurement inaccuracy which results from process variation leading to target asymmetries. The methods comprise identifying an inaccuracy contribution of process variation source(s) to a measured scatterometry signal (e.g., overlay) by measuring the signal across a range of measurement parameter(s) (e.g., wavelength, angle) and targets, and extracting a measurement variability over the range which is indicative of the inaccuracy contribution. The method may further assume certain functional dependencies of the resulting inaccuracy on the target asymmetry, estimate relative donations of different process variation sources and apply external calibration to further enhance the measurement accuracy.

With the overlay measurements and, specifically, the scatterometry algorithm being very sensitive to process variations, acceptable process variations (which do not affect the device performance) may be wrongly reported as unacceptable overlay errors. Embodiments of the present disclosure reduce this inaccuracy using different overlay algorithms. The disclosed algorithms may use the whole information from the entire relevant spectrum and/or all pupil pixels rather than selecting only the "less inaccurate" pixels (either wavelength or angles). The algorithms may handle one or more process variations.

FIG. 1 is a high level schematic block diagram illustrating ways to reduce inaccuracy 100 arising from process variation 80 in scatterometry overlay measurements, according to some embodiments of the invention. These approaches may be implemented in algorithms as described below, and may be implemented within measurement modules in scatterometry overlay measurement tool or be added-on as additional modules. At least part of the algorithmic steps may be carried out by one or more processors 99.

Measured overlays (OVLs) 95, which are measured over multiple targets 105, are understood to be described as a sum of three terms: $OVL_{measured} = OVL_{accurate} + \text{Inaccuracy} + TMU$, with $OVL_{accurate}$ denoting the physical OVL 90 (up to ambiguity). The TMU ("total measurement uncertainty") term consists of the precision, tool induced shift and tool matching, and is henceforth neglected. In scatterometry OVL measurements, the per-pixel OVL, $\epsilon$, may be measured either as a function of the measurement wavelength or as a function of the angle in angle resolved scatterometry. The per-pixel OVL thus may be expressed as real overlay 90 plus inaccuracy 100 (or per-pixel inaccuracy) expressing target asymmetry due to process variation 80, i.e., $\epsilon(p, \text{site}) = OVL(\text{site}) + \text{Inaccuracy}(p, \text{site})$ with p being the pixel index. In the case of multiple targets measured on a wafer, $\epsilon$ can be further approximated as expressed in Equation 1 relating to one process variation:

$$\epsilon(p,\text{site}) = OVL(\text{site}) + A_p \zeta_{site} \quad \text{Equation 1}$$

or as expressed in Equation 2 when relating to N process variations (i.e., when the inaccuracy is caused by a plurality of n process variation sources):

$$\epsilon(p,\text{site}) = OVL(\text{site}) + \sum_{n=1}^{N} A_{p,n} \zeta_{site,n} \quad \text{Equation 2}$$

In these expressions, the OVL inaccuracy is described as a product of the target's asymmetry $\zeta$ (target (defect) property 120), and the pixel response per unit asymmetry A 110. The first term $A_p$ in the product is common for all targets while the second term $\zeta_{site}$ is common for all pixels. This formulation is hence a linear approximation which neglects possible coupling between pixels (for example, due to diffractions) and any nonlinear responses that become irrelevant when the process variation which is moderate.

Statistical analysis 140 may be applied on measurements 105 of multiple targets to derive pixel response 110 to one or more parameters of process variation (Equations 1, 2 and Equations 4, 5) and to quantify target asymmetry 120.

A calibration factor (in the case of a linear approximation) or a calibration function 115 (in the case of non-linear approximations) may be calculated or approximated by applying measurements under varied measurement conditions 130, e.g., with respect to illumination parameters such as wavelengths and directions, and/or using external calibration 150 of target asymmetry, e.g., using a calibration target template. Any of the analysis, estimation and calibration operations may be carried out by processor(s) 99. Methods described in U.S. Patent Publication No. 2014/0060148 are considered part of the present disclosure with respect to deriving calibration factor(s) or function(s) 115.

The disclosed algorithms may be expanded, in certain embodiments, to handle more complex approximations for the inaccuracy (linear approximation is presented here for the sake of clarity, and is non-limiting). In certain embodiments, the disclosed algorithms may be applied to signal other than overlay, for example to the raw reflectivity signal or to differential signals.

Figure 2:
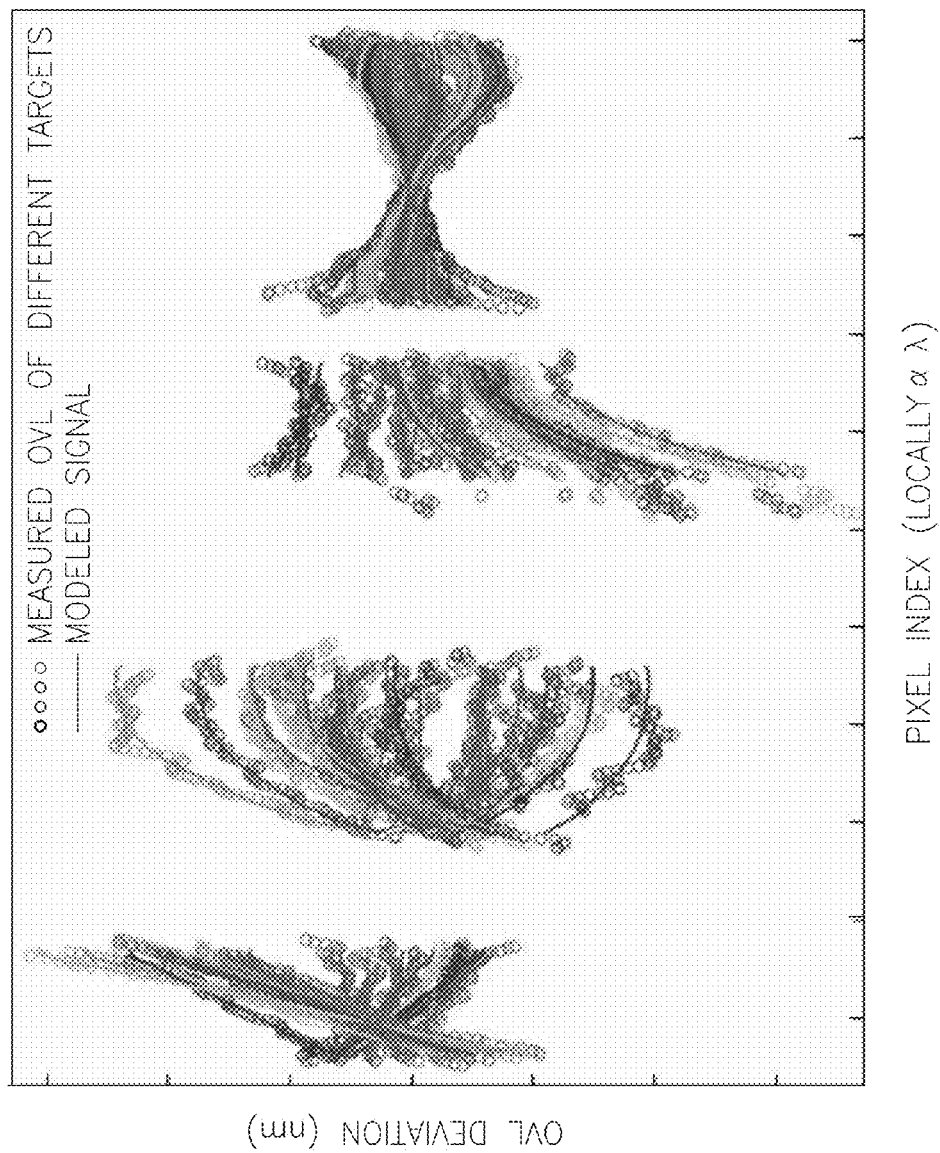
FIG. 2 represents experimental data showing the behavior of the measured per-pixel overlay deviations for different targets in terms of wavelength units, and respective model approximation, according to some embodiments of the invention.

FIG. 2 represents experimental data showing the behavior of the measured per-pixel overlay deviations (in nm, defined as the per-pixel OVL minus the target's OVL, which is the (possibly weighted) average of the per-pixel OVL, various weighting functions may be used to assign pixel weights) for different targets in terms of wavelength units (presented on the x axis as the pixel index which is locally proportional to the wavelength). The figure serves illustrative purposes and hence no exact dimensions are presented. FIG. 2 further illustrates respective model approximations according to some embodiments of the invention. The illustrated dots represent measurements of each target, different targets represented by different shades of grey and respective lines which are calculated fits to the dots according to the model defined by Equation 1. The OVL deviations are illustrated in a non-limiting manner as a function of the measurement wavelength. FIG. 2 illustrates that there is a correlation between the different targets deviations across large portions of the measurement spectrum.

In case of a single process variation, the pixel response to asymmetry may be found, in a non-limiting manner, by assuming that the average inaccuracy of a pixel across the wafer is zero and thus reaching Equation 3:

$$\frac{1}{N_{sites}} \sum_{sites} [\varepsilon(p, site) - OVL(site)] \cdot P_{site} = \quad \text{Equation 3}$$

$$\frac{1}{N_{sites}} \Sigma_{sites} A_p \zeta P_{site} = \frac{1}{N_{sites}} A_p \Sigma_{sites} \zeta P_{site} = A_p \langle \zeta \rangle = \tilde{A}_\gamma$$

$P_{site}$ is a weighting function and $\zeta$ is the average "wafer asymmetry", which is unknown but common for all wavelengths. Different weights may be applied to different sites and targets, to different measurement parameters (e.g., wavelength or angle ranges, which may be described by respective pixel distributions of the varied measurement parameters, e.g., or pupil plane pixels for angles) and to different sources of inaccuracy (see statistical analysis of process variation sources below) to enhance the estimation of the inaccuracy due to process variation and target asymmetry.

In order to eliminate the inaccuracy term using this model, some samples may be measured. The per-pixel inaccuracy response to asymmetry may be found e.g., using Equation 3 or by finding the function that best describes the per-pixel OVL deviations according to Equation 1. Using such a function may allow extracting more accurate OVL values by fitting each target's per-pixel OVL deviations to the response function, as illustrated schematically in FIG. 3.

Figure 3:
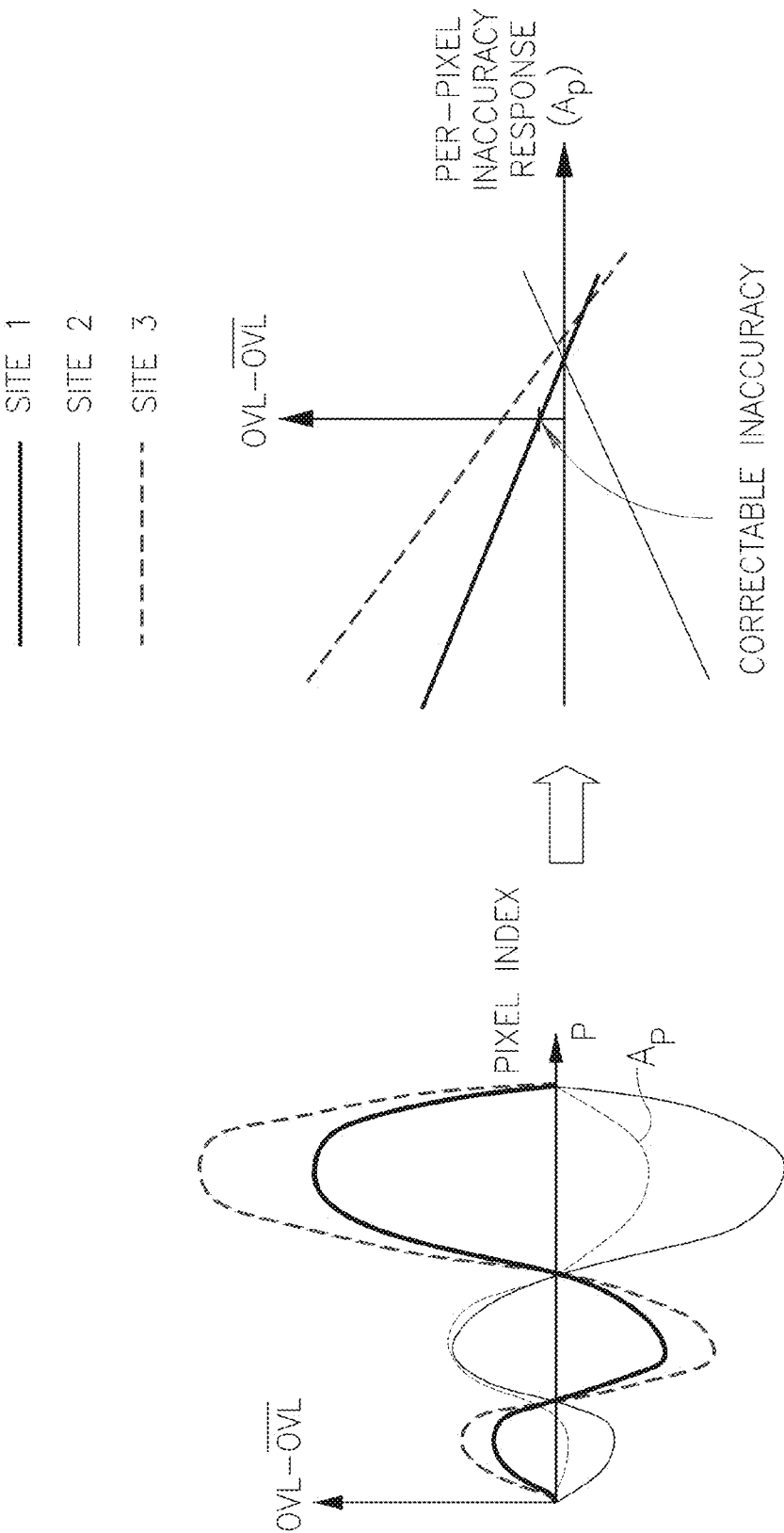
FIG. 3 schematically illustrates overlay deviations for three different targets as a function of pixel index which represents either the wavelength (in wavelength resolved scatterometry) or the pupil angle (in angle resolved scatterometry) in the left figure, and the respective overlay deviations as a function of the "per-pixel inaccuracy response" $A_p$ in the right figure, according to some embodiments of the invention.

FIG. 3 schematically illustrates OVL deviations (OVL−average OVL) for three different targets as a function of pixel index which represents, in a non-limiting manner, either the wavelength (in wavelength resolved scatterometry) or the pupil angle (in angle resolved scatterometry) in the left figure, and the respective overlay deviations as a function of the "per-pixel inaccuracy response" $A_p$ in the right figure. In the latter, it is noted that the OVL inaccuracy may be calibrated for targets having a non-zero overlay for $A_p=0$.

Figure 4:
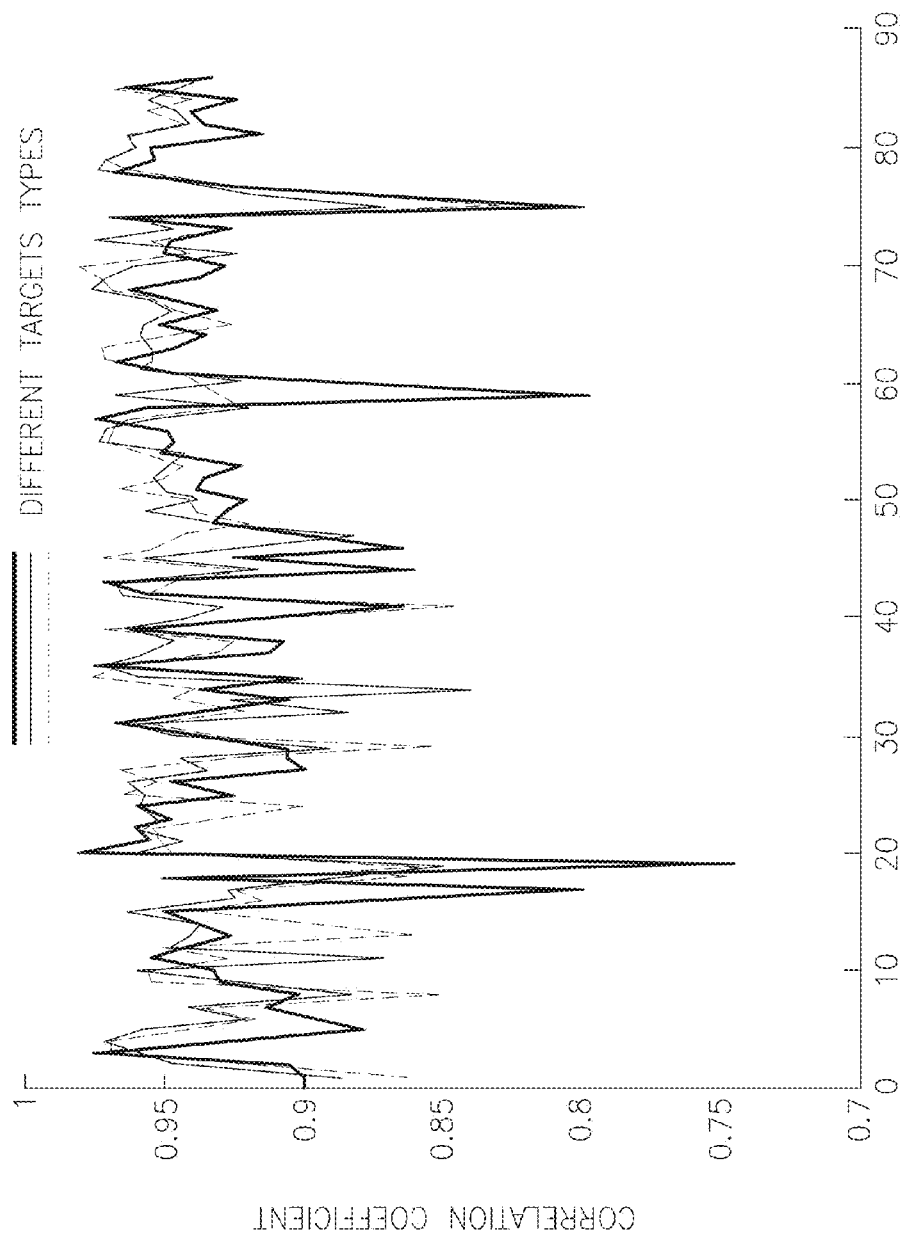
FIG. 4 represents experimental data depicting a correlation between the per-pixel (per angle) overlay deviations of different sites and the average (over wafer) overlay deviations as a function of the site for three different target types, according to some embodiments of the invention; and, FIG. 5 is a high level flowchart illustrating a method according to some embodiments of the invention.

The disclosed methods and algorithms may be applied for angle resolved scatterometry as well. FIG. 4 represents experimental data depicting a correlation between the per-pixel (per angle) OVL deviations of different sites and the average (over wafer) OVL deviations as a function of the site for three different target types. The correlation is typically strong, above 0.9, illustrating that a common "inaccuracy response function" is present (all pixels have similar behavior as a function of sites).

In certain embodiments, the disclosed algorithms may be used to estimate the inaccuracy of each target and measurement conditions, or of the whole wafer and/or be used to monitor the process stability by monitoring the average inaccuracy and the changes in the systematic behavior.

Advantageously, embodiments of the disclosed algorithms comprise the following new and advantageous aspects: (i) The modeling of the per-pixel OVL response to target imperfections based on the "per pixel OVL deviations" and measurement of multiple (regular) OVL targets, sparing the typical need for using simulation tools such as RCWA (Rigorous coupled-wave analysis) and\or extraction of wafer parameters and\or special targets and measurements; (ii) some embodiments provide, on the fly, quantitative inaccuracy estimations on the target level and on the wafer level without requiring additional measurements; (iii) the process may be monitored using quantitative inaccuracy estimation (in nm) rather than qualitative estimation of process variations; (iv) some embodiments enable spectrum selection based on the systematic behavior of the OVL over the wafer, e.g., pixels may be selected in which the OVL deviations correlate; and (v) an estimation of the target quality ("asymmetry index") with respect to other targets is provided.

Turning now to embodiments of the invention, which concern more than one process variation, Equation 2 is rewritten as:

$$\epsilon(p,\text{site}) = OVL(\text{site}) + \Sigma_{n=1}^{N} A_{p,n} \zeta_{site,n} \quad \text{Equation 2}$$

with n being the (effective) process variation index.

The spectral response for these process variations may be found using statistical analysis such as, for example, Principle Components (PC) Analysis. A matrix M is constructed from all the correlations between the different measurements of a given wafer (this can be a production wafer or a cluster of specially designed wafer\s in which controlled process variation\s was\were applied). For example, these matrix elements are expressed in Equation 4, with i and j being the site indexes:

$$M(i, j) = \frac{cov(\varepsilon(p, i), \varepsilon(p, j))_p}{\sqrt{var(\varepsilon(p, i))_p \cdot var(\varepsilon(p, j))_p}} \quad \text{Equation 4}$$

The eigenvectors of this matrix are used to construct the PC vectors in the pixels' space (each eigenvector element is the linear combination coefficient of the corresponding site's per-pixel OVL vector $\epsilon$). The eigenvalues represent the covariance between the PC vectors and the original measurements. The trace of the diagonal matrix (sum of eigenvalues) is one. If some eigenvalues are much bigger than all others, it means that there is correlation between the different measurements, and therefore the measurements can be described using less information. In the formulation of Equation 2, it means that N is smaller than the number of sites. Furthermore, Equation 2 process variation vectors $A_{p,n}$, can be the above PC vectors (or some linear combination of these vectors). The parameter $\zeta_{site,n}$ is the projection of $\epsilon$(site) on the n'th process variation vector.

The measurement inaccuracy is the (weighted) average of the pixels inaccuracy:

$$\text{Inaccuracy(site)} = \langle \Sigma_{n=1}^N A_{p,n} \cdot \zeta_{site,n} \rangle_p = \Sigma_{n=1}^N \zeta_{site,n} \cdot \langle A_{p,n} \rangle_p \quad \text{Equation 5}$$

Since the PC assumes that $(A_{p,n})_p = 0$, the vector averages should be found using additional method. Such a method is described, for example, in U.S. Patent Publication No. 2014/0060148, which is incorporated herein by reference in its entirety.

U.S. Patent Publication No. 2014/0060148 discloses systems and methods for calibrating a metrology tool by using proportionality factors. The proportionality factors may be obtained by measuring a substrate under different measurement conditions, and then calculating the measured metrology value and one or more quality merits. From this information, proportionality factors may be determined. Thereafter, the proportionality factors may be used to quantify the inaccuracy in a metrology measurement. The proportionality factors may also be used to determine an optimize measurement recipe. Any combination of embodiments of the present invention and aspects of U.S. Patent Publication No. 2014/0060148 is considered part of the present disclosure as well.

In certain embodiments, statistical analysis 140 may be carried out by a variety of known methods, including more complicated methods such as Robust PCA, 2D PCA, Tensor Decomposition or Isomaps.

In certain embodiments, process variation signatures or typical responses may be identified based upon the disclosed models and algorithms, and be used to quantify process variations and inaccuracies of additional measurements, for example, during High Volume Manufacturing; to monitor process stability with respect to the different process variations and/or to identify defective targets and\or outlying measurements ("outliers").

Advantageously, in certain embodiments, the disclosed algorithms extract more information from the wavelength and/or angle ranges (which may be described in pixel terms) with respect to typical scatterometry overlay algorithms by comparing the overlay distribution within the spectrum of a specific target and the systematic behavior between targets rather than averaging these values.

Figure 5:
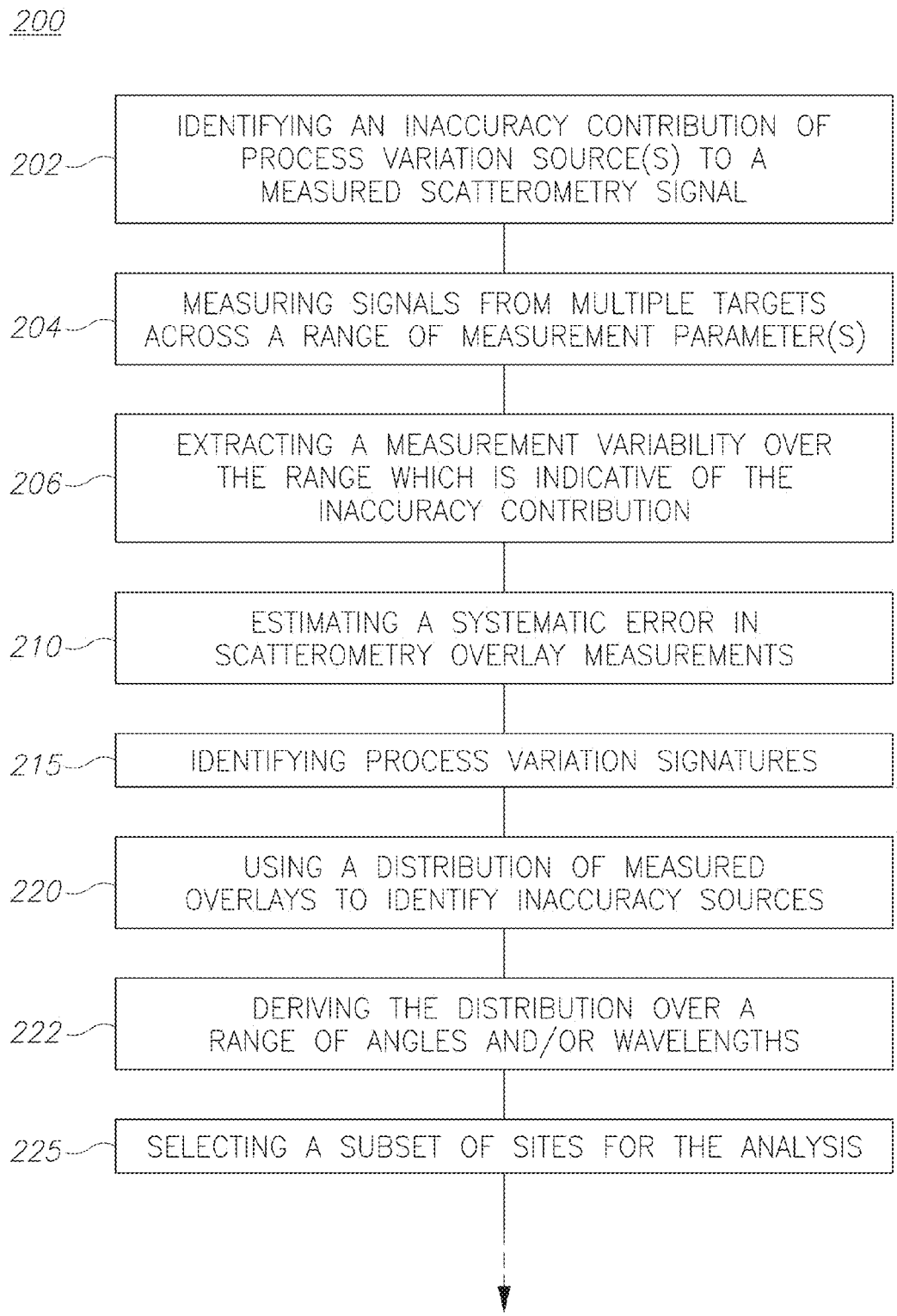

FIG. 5 is a high level flowchart illustrating method 200 according to some embodiments of the invention. Any stage of method 200 may be carried out by at least one processor (stage 270). Certain embodiments comprise computer program products having a computer readable storage medium having computer readable program embodied therewith and configured to perform at least a part of at least one of the following stages.

Method 200 may comprise identifying an inaccuracy contribution of process variation source(s) to a measured scatterometry signal (stage 202), measuring signals from a plurality of targets across a range of measurement parameter(s) (stage 204), and extracting a measurement variability over the range, which is indicative of the inaccuracy contribution (stage 206), using e.g., the model presented in Equations 1, 2 and 4 and its derivations in Equations 3 and 5 respectively.

Method 200 may comprise estimating a systematic error in scatterometry overlay measurements (stage 210) using a distribution of measured overlays to identify inaccuracy sources (stage 220) and deriving at least one inaccuracy source resulting from at least one process variation (stage 230).

In certain embodiments, method 200 may further comprise identifying process variation signatures or typical responses (stage 215). Method 200 may further comprise using the process variation response signatures to quantify process variations and inaccuracies of additional measurements, for example, during High Volume Manufacturing. Method 200 may further comprise monitoring process stability with respect to the different process variations and/or comprising identifying defective targets and\or outlying measurements ("outliers").

In certain embodiments, method 200 may further comprise deriving the distribution over a range of angles and/or wavelengths (stage 222) and possibly selecting a subset of sites for the analysis (stage 225). The ranges may be described in pixel terms, by respective pixel distributions of the varied measurement parameters.

In certain embodiments, method 200 may further comprise modelling the effect of process variation on measured overlays (stage 235) and selecting main inaccuracy sources according to an initial analysis (stage 237).

Method 200 may further comprise estimating, per-pixel and per-site, a donation to measured overlay by the derived sources (stage 240). Method 200 may comprise calibrating the derivation and/or estimation using the model (stage 245) and varying measurement conditions to carry out the calibration (stage 247).

Method 200 may further comprise defining a number of significant inaccuracy sources and/or process variation parameters according to the model, derivation and/or estimation (stage 250). Method 200 may comprise identifying outliers using the model, derivation and/or estimation (stage 252).

Method 200 may further comprise using principle components analysis for any of derivation 230, estimation 210 and/or modelling 235 (stage 260).

Advantageously, embodiments of the disclosed algorithms comprise the following new and advantageous aspects: (i) Finding different process variation signatures using correlations in the overlay distribution across the pupil between different measurements; (ii) Estimating the magnitude of different process variations and their effect on the measurement inaccuracy using the above method; (iii) Monitoring different process variations using overlay measurements; (iv) Optimizing measurement conditions (target design, hardware and\or algorithm) using quantitative inaccuracy estimations; (v) Eliminating measurement inaccuracies from different process variations using quantitative inaccuracy estimation; (vi) Using principle component analysis to find the different process variation signatures in the pupil; and (vii) All the above using correlations in the reflectivity distribution across the pupil between different measurements and/or correlations in the differential signal distribution across the pupil between different measurements.

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A metrology method, comprising the steps of:
measuring, with an overlay scatterometry metrology tool, a signal from each of a plurality of targets across a range of at least one measurement parameter;
identifying, with one or more processors, an inaccuracy contribution of at least one process variation source to the measured scatterometry signal; and
extracting, with the one or more processors, a measurement variability over a range indicative of the inaccuracy contribution by modeling, with the one or more processors, a per-pixel measured overlay response to target imperfections based on per-pixel measured overlay deviations and measurement of multiple overlay targets.

2. The method of claim 1, wherein the signal comprises: at least one of an overlay signal, a raw reflectivity signal, or a differential measurement signal.

3. The method of claim 1, wherein the at least one measurement parameter comprises:
at least one of wavelength or angle, described by terms with respect to pixels.

4. The method of claim 1, further comprising:
identifying at least one process variation signature in the extracted measurement variability.

5. The method of claim 4, further comprising:
quantifying process variations and inaccuracies of additional measurements by using the at least one process variation signature.

6. The method of claim 5, further comprising:
monitoring process stability with respect to the process variations.

7. The method of claim 5, further comprising:
identifying at least one of defective targets or outlying measurements.

8. The method of claim 1, further comprising:
selecting a subset of wafer sites where measurements are acquired.

9. The method of claim 1, further comprising:
applying a linear approximation of a dependency of the inaccuracy on a target asymmetry resulting from the process variation source.

10. The method of claim 1, wherein the inaccuracy is caused by a plurality of process variation sources, wherein the method further comprises
estimating relative contributions of the different process variation sources by applying a statistical analysis.

11. The method of claim 1, further comprising:
selecting a spectrum based on systematic behavior over the wafer, wherein selection of a spectrum includes selecting pixels where the per-pixel measured overlay deviation is correlated to the average measured overlay deviation over a wafer.

12. A system, comprising:
an overlay scatterometry metrology tool;
a memory element configured to store a plurality of computer-readable instructions;
a processor communicatively coupled to the overlay scatterometry metrology tool and configured to execute the plurality of computer-readable instructions to,
direct the overlay scatterometry metrology tool to measure a signal from a plurality of targets across a range of at least one measurement parameter;
identify an inaccuracy contribution of at least one process variation source to a measured scatterometry signal; and
extract a measurement variability over the range indicative of the inaccuracy contribution with a model of a per-pixel measured overlay response to target imperfections based on per-pixel measured overlay deviations and measurement of multiple overlay targets.

13. The metrology system of claim 12, wherein the processor is configured to execute the plurality of computer-readable instructions to identify at least one process variation signature in the extracted measurement variability.

14. The system of claim 13, wherein the processor is configured to execute the plurality of computer-readable instructions to quantify process variations and inaccuracies of additional measurements by using the at least one process variation signature.

15. The system of claim 12, wherein the processor is configured to execute the plurality of computer-readable instructions to monitor process stability with respect to the process variations.

16. The system of claim 12, wherein the processor is configured to execute the plurality of computer-readable instructions to identify at least one of defective targets or outlying measurements.

17. The system of claim 12, wherein the processor is configured to execute the plurality of computer-readable instructions to select a subset of wafer sites for the measuring.

18. The system of claim 12, wherein the processor is configured to execute the plurality of computer-readable instructions to apply a linear approximation of a dependency of the inaccuracy on a target asymmetry resulting from the process variation source.

19. The system of claim 12, wherein the processor is configured to execute the plurality of computer-readable instructions to select a spectrum based on systematic behavior over the wafer, wherein selection of a spectrum includes selecting pixels where the per-pixel measured overlay deviation is correlated to the average measured overlay deviation over a wafer.

* * * * *